United States Patent [19]
Coffen et al.

[11] 3,932,399
[45] Jan. 13, 1976

[54] 2,5-EPITHIO-1,4-BENZODIAZEPINES

[75] Inventors: David Llewellyn Coffen, Glenridge; Rodney I. Fryer, North Caldwell, both of N.J.

[73] Assignee: Hoffmann-La Roche Inc., Nutley, N.J.

[22] Filed: Aug. 28, 1974

[21] Appl. No.: 501,303

Related U.S. Application Data

[62] Division of Ser. No. 383,362, July 27, 1973, Pat. No. 3,850,948.

[52] U.S. Cl. ............................ 260/243 R; 424/246
[51] Int. Cl.² ...................................... C07D 513/08
[58] Field of Search .................. 260/239 BD, 243 R

[56] References Cited
UNITED STATES PATENTS

| | | | |
|---|---|---|---|
| 3,481,921 | 12/1969 | Field et al. | 260/239 BD |
| 3,856,787 | 12/1974 | Steinman | 260/243 R |

OTHER PUBLICATIONS

Sternbach et al., Symposium on CNS Drugs, Hyderbad, India, CSIR, New Delhi, India, 1966.
Knollmueller, Chem. Abstracts, Vol. 75, Abstract No. 129776K (1971).

*Primary Examiner*—Alton D. Rollins
*Attorney, Agent, or Firm*—Samuel L. Welt; Bernard S. Leon; Frank P. Hoffmann

[57] ABSTRACT

Novel 1,4-benzodiazepine derivatives, bearing between positions 1- and 2- a thiazolo or oxathiazepino ring, methods for their preparation and novel intermediates employed in these processes are disclosed. These 1,2-heterocyclic-1,4-benzodiazepines are useful as muscle-relaxant, anti-convulsant and sedative agents.

3 Claims, No Drawings

2,5-EPITHIO-1,4-BENZODIAZEPINES

This is a division, of application Ser. No. 383,362 filed July 27, 1973, now U.S. Pat. No. 3,850,948.

DETAILED DESCRIPTION OF THE INVENTION

The present invention relates to novel 1,4-benzodiazepine derivatives bearing between positions 1- and 2- a sulfur containing heterocyclic ring. More particularly, this invention covers 1,4-benzodiazepines bearing a thiazolo or oxathiazepino ring between the 1-and 2-positions. The invention further comprehends processes for making these novel benzodiazepines and novel intermediates employed in these processes.

More specifically, the compounds of the present invention are selected from the group consisting of compounds of the formula

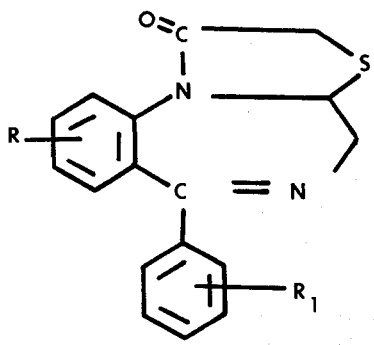

I and of the formula

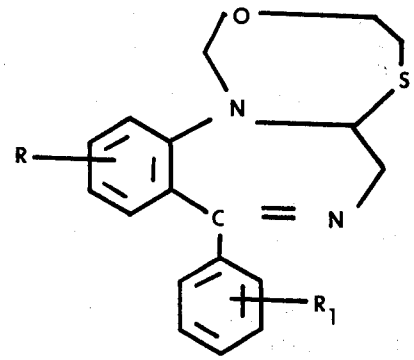

II wherein R is selected from the group consisting of hydrogen, halogen, lower alkyl, trifluoromethyl, nitro, cyano, lower alkoxy and lower alkylthio; $R_1$ signifies hydrogen or halogen and the pharmaceutically acceptable acid addition salts thereof.

As used herein, the term "lower alkyl" either alone or in combination refers to straight and branched chain hydrocarbon groups containing from 1 to 7, preferably from 1 to 4, carbon atoms; such as, for example, methyl, ethyl, propyl, isopropyl, isobutyl, butyl and the like. The term "halogen" refers to all four forms thereof, i.e. bromine, chlorine, fluorine and iodine. The term "lower alkoxy" designates straight or branched chain saturated hydrocarbonoxy groups containing from 1 to 7 carbon atoms, preferably from 1 to 4 carbon atoms, such as methoxy, ethoxy, propoxy and the like.

Preferred among the compounds falling within the scope of formula I or II above are those wherein R signifies halogen or nitro and is located in the 7-position of the basic benzodiazepine moiety, and $R_1$ is located at the ortho-position of the 5-phenyl ring in the basic benzodiazepine moiety, i.e. compounds of the formula

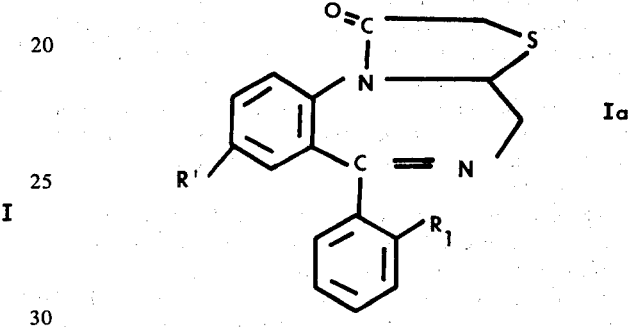

Ia and of the formula

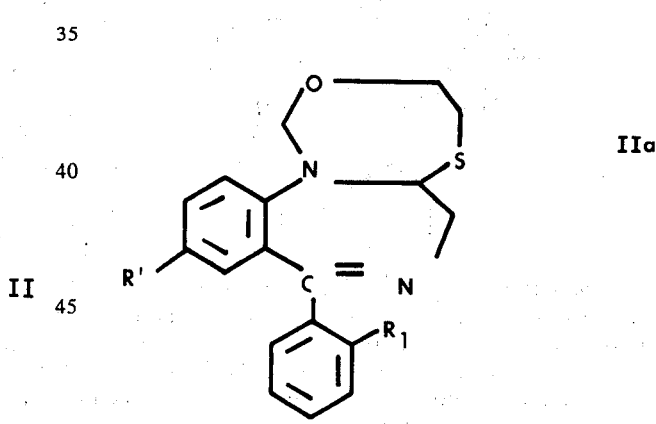

IIa wherein R' signifies halogen or nitro and $R_1$ is as described above.

When the R substituent signifies halogen, chlorine is preferred, while when $R_1$ signifies halogen, chlorine and fluorine are preferred.

The most preferred of the compounds of formulae I and II above are: 3a,4-dihydro-8-chloro-6-phenyl-thiazolo[3,2-A]-1,4-benzodiazepin-1(2H)-one and 10-chloro-3,4,5a, 6-tetrahydro-8-phenyl-1H-1,5,3-oxa-thiazepino[3,4-A]-1,4-benzodiazepine.

The compounds of the present invention can be prepared as described below. Thus, the compounds of formula I above may be prepared by treating the corresponding 3H-1,4-benzodiazepine of the formula

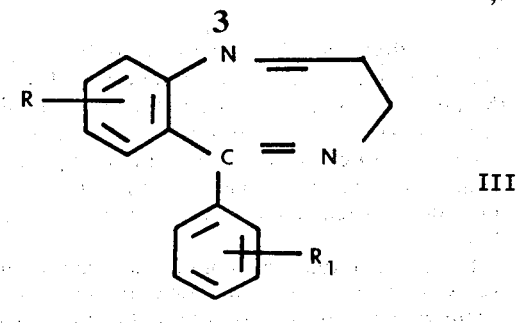

III wherein R and R₁ are as described above
with mercaptoacetic acid. The reaction between the benzodiazepine starting material of formula III and mercaptoacetic acid is preferably effected in the presence of a non-nucleophilic inert organic solvent. Suitable solvents for this purpose include ethers, such as tetrahydrofuran, aromatic hydrocarbons such as benzene, toluene and xylene, halogenated aliphatic hydrocarbons such as methylene chloride, chloroform and the like. Temperature is not critical to this process aspect so that temperatures in the range of from room temperature to the reflux temperature of the reaction mixture can be employed, with reflux temperature being preferred.

The starting materials of formula III above are known compounds or can be prepared in analogy to the preparation of the known compounds.

In an alternate synthetic approach, the compounds of formula I above can be prepared by reacting a 2,5-epithio-1,4-benzodiazepine of the formula

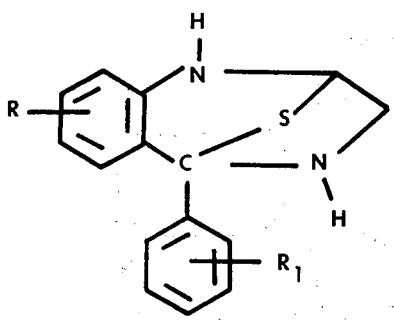

IV wherein R and R₁ are as described above
with mercaptoacetic acid. The reaction conditons employed in the reaction between the compound of formula IV above and mercaptoacetic acid are the same as those described above for the reaction of the compound of formula III with mercaptoacetic acid.

The compounds of formula IV above used as the starting materials in this alternate synthetic approach to the desired end products of formula I can be prepared by bubbling hydrogen sulfide into a solution of a benzodiazepine of formula III above. Suitable solvents for this purpose include non-nucleophilic inert organic solvents such as ethers, for example, tetrahydrofuran, aromatic hydrocarbons such as benzene, toluene, xylene, cyclohexane and the like, halogenated aliphatic hydrocarbons such as methylene chloride, chloroform and the like.

The compounds of formula IV above are novel and as such form a part of the present invention. These compounds are not only useful as intermediates in the preparation of the compounds of formula I as described above or the compounds of formula II as described hereinafter, but are useful in themselves as sedative, muscle relaxant and anti-convulsant agents.

In a further process aspect the compounds of formula III above may be used as the starting materials in the preparation of the desired end products of formula II.

Following this preparative approach, the compounds of formula III are first treated with 2-mercaptoethanol to yield the 2-hydroxyethylthio-1,4-benzodiazepine of the formula

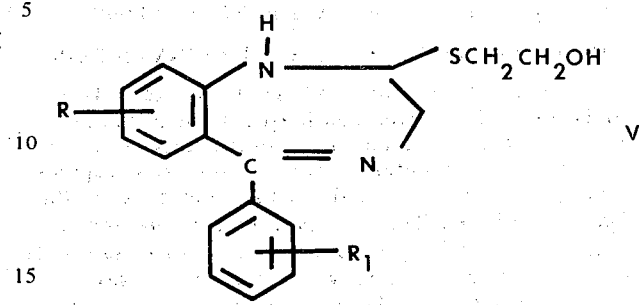

V wherein R and R₁ are as described above

The compounds of formula V above are novel and as such form a part of the present invention. These compounds are not only useful as intermediates in the preparation of the compounds of formula II above, but are also active themselves as musclerelaxant, anticonvulsant and sedative agents.

The so-obtained compounds of formula V above are then reacted with aqueous formaldehyde to yield the desired end products of formula II. The reaction between the compound of formula V above and aqueous formaldehyde is preferably effected in the presence of an inert organic solvent. Suitable solvents for this purpose include ethers such as tetrahydrofuran, alkanols such as methanol, ethanol, propanol and the like and aromatic hydrocarbons such as benzene, toluene, xylene and the like. Temperature is not a critical aspect to this process and thus the reaction is preferably effected at room temperature. The intermediate of formula V above used in the preparation of the formula II compound can also by prepared by treating the 2,5-epithio-1,4-benzodiazepine of formula IV above with mercaptoethanol. The reaction between the compound of formula IV above and mercaptoethanol is preferably effected in the presence of an inert non-nucleophilic organic solvent. Suitable solvents include ethers such as tetrahydrofuran, aromatic hydrocarbons such as benzene, toluene, xylene and the like, halogenated aliphatic hydrocarbons such as methylene chloride and chloroform. This reaction is expediently effected at elevated temperatures, preferably at the reflux temperature of the reaction mixture.

The compounds of formulae I, II, IV and V above form pharmaceutically acceptable acid addition salts with organic and inorganic acids. Thus the compounds of the present invention form pharmaceutically acceptable acid addition salts with inorganic acids such as the hydrohalic acids, for example hydrochloric acid and hydrobromic acid, and with organic acids such as tartaric acid, citric acid, camphor sulfonic acid, ethane sulfonic acid, toluene sulfonic acid, salicylic acid, ascorbic acid, maleic acid, succinic acid, formic acid, acetic acid and the like.

The compounds of formula I above as well as their pharmaceutically acceptable acid addition salts are useful as anticonvulsant agents, while the compounds of formulae II, IV and V above are useful as anti-convulsant, muscle relaxant and sedative agents. Thus, the compounds of the present invention and their pharmaceutically acceptable salts can be used as medicaments. For example, they can be used in the form of pharmaceutical preparations which contain them or their salts in ad-mixture with a pharmaceutical organic or inorganic carrier material which is suitable for enteral or parenteral application such as, for example, water, gelatin, lactose, starches, magnesium sterate, talc, vegetable oils, gum arabic, polyalkyleneglycols, vaseline, etc. The pharmaceutical preparations can be prepared in solid form (e.g. as tablets, dragees, suppositories, capsules) or in liquid form (e.g. as solutions, suspensions or emulsions). They may be sterilized and/or contain additives such as preserving, stabilizing, wetting or emulsifying agents, salts for varying the osmotic pressure or buffers. They can also contain other therapeutically valuable substances.

The compounds of formulae I, II, IV and V above or their pharmaceutically acceptable salts can be administered at dosages adjusted to individual requirements and fitted to the pharmaceutical exigencies of the situation. Convenient pharmaceutical dosages are in the range of from about 2 mg. to about 200 mg. per day.

The useful anticonvulsant activity of the compounds of formulae I, II, IV and V above is shown in warm blooded animals utilizing the standard antimetrazole test. This test was carried out according to the method of Everett and Richard (J.P.E.T., 81: 402, 1944). The $ED_{50}$ was calculated as the dose which would prevent convulsions in 50% of the mice tested after administration of 125 mg/kg of pentylenetetrazole by the subcutaneous route. Following these test procedures compounds such as: 3a,-4-dihydro-8-chloro-6-phenyl-thiazolo[3,2-A]-1,4-benzodiazepin-1(2H)-one (Compound A), 7-chloro-2,3-dihydro-2-(2-hydroxyethylthio)-5-phenyl-1H-1,4-benzodiazepine (Compound B), 10-chloro-3,4,5a,6-tetrahydro-8-phenyl-1H-1,5,3-oxathiazepino[3,4-A]-1,4-benzodiazepine(Compound C), and 7-chloro-2,3,4,5-tetrahydro-5-phenyl-2,5-epithio-1H-1,4-benzodiazepine (Compound D) show an $ED_{50}$ of 137±23, 3.22±0.35, 5.4±1.0 and 6.0 mg/kg respectively, indicating that these compounds exhibit anticonvulsant activity.

The sedative and muscle relaxant activity of the compounds of formulae II, IV and V above are shown using the standard foot shock test. In this test a pair of mice is confined under a 1 liter beaker placed on a grid which presents elicited to the feet. At least five fighting episodes are elicitated in a two minute period. Pairs of mice are marked and pretreated 1 hour prior to a second shock. Logarithmic dose intervals are utilized up to a maximum of 10 mg/kg. At the 100% blocking dose, three out of three pairs must be blocked from fighting. The measurements are made at the dose level at which 100% blocking is observed and the results are expressed as the dose in mg/kg ($PD_{50}$) which blocks the fighting response for 1-hour. Following these test procedures, compound B exhibited a $PD_{50}$ of 10 mg/kg, compound C exhibited a $PD_{50}$ of 50 mg/kg, and compound D exhibited a $PD_{50}$ of 50 mg/kg, indicating that these compounds exhibit sedative and muscle-relaxant activity.

The following examples are illustrative of the present invention. All temperatures are given in degrees Centigrade.

EXAMPLE 1

Preparation of 7-chloro-5-(2-fluorophenyl)-2,3,4,5-tetrahydro-2,5-epithio-1H-1,4-benzodiazepine.

A mixture of manganese dioxide (General Metallic Oxides, Type No. 37) (50 g) in benzene (500 ml) was heated and stirred under reflux while collecting water in a Dean-Stark trap. After 1 hr, 7-chloro-2,3-dihydro-5-(2-fluorophenyl)-1H-1,4-benzodiazepine (5 g) and acetic acid (17 ml) were added and stirring under reflux was continued for an additional hour. Tlc analysis of the reaction mixture at this point established that the oxidation was complete. The manganese dioxide was filtered out and washed with a 1:1 mixture of ethanol and methylene chloride. The combined filtrate and washings was washed with aqueous sodium carbonate solution and with water, dried and evaporated to leave an oily residue.

The residue was taken up in tetrahydrofuran (150 ml) and hydrogen sulfide gas was bubbled through the stirred solution for 1½ hr. The solvent was evaporated and the residue taken up in methylene chloride, decolorized with charcoal and concentrated with addition of petroleum ether until the product began to crystallize. In this manner the above-named product was obtained as pale yellow crystals, mp 124°–127°.

EXAMPLE 2

Preparation of 7-chloro-2,3,4,5-tetrahydro-5-phenyl-2,5-epithio-1H-1,4-benzodiazepine.

A stirred solution of crude 7-chloro-5-phenyl-3H-1,4-benzodiazepine obtained from the oxidation of 7-chloro-2,3-dihydro-5-phenyl-1H-1,4-benzodiazepine (120 g) with manganese dioxide in THF (1 l.) was saturated with hydrogen sulfide gas for 1½ hours. The solvent was evaporated and the solid residue triturated with ether, filtered and washed with ether to give the above-named product as a colorless powder. Crystals from methylene chloride/ether had mp 142°–144° (dec).

EXAMPLE 3

Preparation of 7-chloro-2,3-dihydro-2-(2-hydroxyethylthio)-5-phenyl-1H-1,4-benzodiazepine.

7-chloro-2,3-dihydro-5-phenyl-1H-1,4-benzodiazepine (10 g) was oxidized to 7-chloro-5-phenyl-3H-1,4-benzodiazepine as described in Example 1 with the addition of 0.1 ml of acetic acid. The crude oxidation product was taken up in THF (60 ml), treated with 2-mercaptoethanol (10 ml) and heated under reflux overnight. The resulting solution was concentrated under reduced pressure until the product began to crystallize and then diluted with 100 ml of ether. The product was collected and washed with ether to give the above-named product as colorless crystals, mp 135°–140° (dec).

EXAMPLE 4

Preparation of 10-chloro-3,4,5a, 6-tetrahydro-8-phenyl-1H-1,5,3-oxathiazepino[3,4-a]-1,4-benzodiazepine.

7-chloro-2,3-dihydro-2-(2-hydroxyethylthio)-5-phenyl-1H-1,4-benzodiazepine (500 mg) in THF (10 ml) was treated with 37% aqueous formaldehyde solution (2 ml) and kept for 5 hours.

Dilution with water while scratching induced crystallization of a yellow solid. Recrystallization from methylene chloride/ether gave the above-named product as pale yellow prisms, mp 160°–164°.

EXAMPLE 5

Preparation of
3a,4-Dihydro-8-chloro-6-phenylthiazolo[3,2-a]-1,4-benzodiazepin-1(2H)-one.

Crude 7-chloro-5-phenyl-3H-1,4-benzodiazepine from the oxidation of 7-chloro-2,3-dihydro-5-phenyl-1H-1,4-benzodiazepine (15 g) in benzene (1 l.) was treated slowly with excess mercaptoacetic acid (15 ml) and then stirred and heated under reflux for 23 hr. The cooled solution was washed with aqueous sodium carbonate, dried, evaporated, and the oily residue taken up in ether. A mixture of the above-named product and the bis-thiazolo compound { 2-chloro-8a,9-dihydro-13a-phenyl-13aH-bis-thiazolo-[4,5-a:3',2'-d]-1,4- benzodiazepin-6,11 (7H,12H)-dione } which is also formed during the reaction crystallized out on standing. Chromatography of this mixture on 500 g of silica gel with hexane/ethyl acetate mixtures as eluent provided, after a recrystallization from methylene chloride/methanol, the desired end product named above, which is the more polar substance. This product was obtained as pale yellow crystals mp 228°–230°.

EXAMPLE 6

Preparation of
7-chloro-2,3-dihydro-2-(2-hydroxyethylthio)-5-phenyl-1H-1,4 -benzodiazepine.

A solution of 7-chloro-2,3,4,5-tetrahydro-5-phenyl-2,5-epithio-1H-1,4-benzodiazepine (1g.) and 2-mercaptoethanol (1 ml) in THF (15 ml) was heated under reflux overnight. The resulting solution was concentrated under reduced pressure and then diluted with ether to induce crystallization of the product. The product was filtered out and washed with ether to give the above-named compound, m.p. 135°–140° (dec.).

EXAMPLE 7

Preparation of 3a,4-dihydro-8-chloro-6-phenylthiazolo [3,2-a] -1,4- benzodiazepin-1(2H)-one.

A solution of 7-chloro-2,3,4,5-tetrahydro-5-phenyl-2,5-epithio-1H-1,4-benzodiazepine (500 mg) in THF was treated slowly with excess mercaptoacetic acid (0.5 ml) and stirred and heated under reflux for 16 hours. The cooled solution was washed with aqueous sodium carbonate, dried, evaporated, and the oily residue taken up in ether. The desired product was re-crystallized from methylene chloride/methanol and was obtained as pale yellow crystals, m.p. 228°–230°.

EXAMPLE 8

Capsule Formulation

|  | Per Capsule |
|---|---|
| 3a,4-Dihydro-8-chloro-6-phenylthiazolo-[3,2-a]-1,4- benzodiazepin-1(2H)-one | 50 mg |
| Lactose, USP | 125 mg |
| Corn Starch, USP | 30 mg |
| Talc, USP | 5 mg |
| Total Weight | 210 mg |

Procedure:

1. The drug was mixed with lactose and corn starch in a suitable mixer.
2. The mixture was further blended by passing through a Fitzpatrick Comminuting machine with a No. 1A screen with knives forward.
3. The blended powder was returned to the mixer, the talc added and blended thoroughly.
4. The mixture was filled into No. 4 hard shell gelatin capsules on a Parke Davis capsulating machine.

EXAMPLE 9

Capsule Formulation

Capsule Formulation

|  | Per Capsule |
|---|---|
| 3a,4-Dihydro-8-chloro-6-phenylthiazolo-[3,2-a]-1,4- benzodiazepin-1(2H)-one | 10 mg |
| Lactose | 158 mg |
| Corn Starch | 37 mg |
| Talc | 5 mg |
| Total Weight | 210 mg |

Procedure:

1. The drug was mixed with the lactose and corn starch in a suitable mixer.
2. The mixer was further blended by passing through a Fitzpatrick Comminuting machine with a No. 1A screen with knives forward.
3. The blended powder was returned to the mixer, the talc added and blended thoroughly. The mixture was then filled into No. 4 hard shell gelatin capsules on a Parke Davis capsulating machine. (Any similar type machine may be used).

EXAMPLE 10

Tablet Formulation

|  | Per Tablet |
|---|---|
| 3a,4-Dihydro-8-chloro-6-phenylthiazolo-[3,2-a] -1,4- benzodiazepin-1(2H)-one | 25.00 mg |
| Lactose, USP | 64.50 mg |
| Corn Starch | 10.00 mg |
| Magnesium Stearate | 0.50 mg |
| Total Weight | 100.00 mg |

Procedure:

1. The drug was mixed with the lactose, corn starch and magnesium stearate in a suitable mixer.
2. The mixture was further blended by passing through a Fitzpatrick Comminuting machine fitted with a No. 1A screen with knives forward.
3. The mixed powders were slugged on a tablet compressing machine.
4. The slugs were comminuted to a mesh size (No. 16 screen) and mixed well.
5. The tablets were compressed at a tablet weight of 100 mg using tablet punches having a diameter of approximately ¼ inch. (Tablets may be either flat or biconvex and may be scored if desired).

EXAMPLE 11

Tablet Formulation

Tablet Formulation

|  | Per Tablet |
|---|---|
| 3a,4-Dihydro-8-chloro-6-phenylthiazolo-[3,2-a] -1,4- benzodiazepin-1(2H)-one | 10.0 mg |
| Lactose | 113.5 mg |
| Corn Starch | 70.5 mg |
| Pregelatinized Corn Starch | 8.0 mg |
| Calcium Stearate | 3.0 mg |
| Total Weight | 205.0 mg |

9

Procedure:

1. The drug was mixed with the lactose, corn starch and pregelatinized corn starch in a suitable size mixer.
2. The mix was passed through a Fitzpatrick Comminuting machine fitted with No. 1A screen and with knives forward.
3. The mix was returned to the mixer and moistened with water to a thick paste. The moist mass was passed through a No. 12 screen and the moist granules were dried on paper lined trays at 110°F.
4. The dried granules were returned to the mixer, the calcium stearate was added, and mixed well.
5. The granules were compressed at a tablet weight of 200 mg using standard concave punches having a diameter of 5/16 inch.

EXAMPLE 12

The formulations set forth in Examples 8–11 above can be prepared, incorporating the following compounds as the active ingredients:

7-chloro-2,3-dihydro-2-(2-hydroxyethylthio)-5-phenyl-1H-1,4-benzodiazepine and 10-chloro-3,4,5A,6-tetrahydro-8-phenyl-1H-1,5,3-Oxathiazepino[3,4-H]-1,4-benzodiazepine.

We claim:

1. A compound of the formula

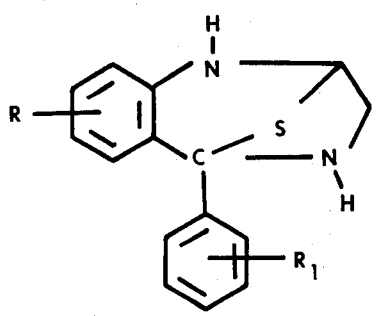

wherein R is selected from the group consisting of hydrogen, halogen, lower alkyl, trifluoromethyl, nitro, cyano, lower alkoxy and lower alkylthio; $R_1$ signifies hydrogen or halogen
and the pharmaceutically acceptable acid addition salts thereof.

2. The compound of claim 1 of the formula 7-chloro-2,3,4,5-tetrahydro-5-phenyl-2,5-epithio-1H-1,4-benzodiazepine.

3. The compound of claim 1 of the formula 7-chloro-5-(2-fluorophenyl)-2,3,4,5-tetrahydro-2,5-epithio-1H-1,4-benzodiazepine.

* * * * *